(12) United States Patent
Louis et al.

(10) Patent No.: US 11,717,585 B2
(45) Date of Patent: *Aug. 8, 2023

(54) SCRUBBING DEVICE FOR CLEANING, SANITIZING OR DISINFECTING

(71) Applicant: GOJO Industries, Inc., Akron, OH (US)

(72) Inventors: Jeffrey S. Louis, Akron, OH (US); Tsung-Chan Tsai, Worthington, OH (US); Daphne Pappas Antonakas, Hudson, OH (US); David Petrak, Aurora, OH (US); Sameer Kalghatgi, Cherry Hill, NJ (US); Robert L. Gray, Kent, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/466,503

(22) Filed: Sep. 3, 2021

(65) Prior Publication Data

US 2021/0393827 A1 Dec. 23, 2021

Related U.S. Application Data

(63) Continuation of application No. 15/747,478, filed as application No. PCT/US2016/044160 on Jul. 27, 2016, now Pat. No. 11,123,446.

(Continued)

(51) Int. Cl.
*A61L 2/14* (2006.01)
*A47L 13/19* (2006.01)
(Continued)

(52) U.S. Cl.
CPC .............. *A61L 2/14* (2013.01); *A47L 13/19* (2013.01); *A47L 13/22* (2013.01); *A47L 13/26* (2013.01);
(Continued)

(58) Field of Classification Search
CPC .......... A47L 13/19; A47L 13/26; A47L 13/22; A47L 2601/03; A47L 2601/02;
(Continued)

(56) References Cited

U.S. PATENT DOCUMENTS

| 3,918,987 A | 11/1975 | Kopfer |
| 4,020,856 A | 5/1977 | Masterson |

(Continued)

FOREIGN PATENT DOCUMENTS

| EP | 1356828 A1 | 10/2003 |
| WO | 0110215 A1 | 2/2001 |

(Continued)

OTHER PUBLICATIONS

International Search Report and Written Opinion from International Application No. PCT/US2013/063360, dated Dec. 11, 2013.

(Continued)

*Primary Examiner* — Benjamin L Osterhout
(74) *Attorney, Agent, or Firm* — Calfee, Halter & Griswold LLP

(57) ABSTRACT

A cleaning, sanitizing or disinfecting scrubbing device includes a body, a non-thermal plasma generator and damp wipe. Generated plasma activates fluid in the wipe. The device may include spacer posts between the body and wipe and a conductive mesh between the body and wipe or embedded in the wipe. Another embodiment includes a reservoir for holding a water-based fluid, a fluid delivery element connected to the reservoir by a tube through which the fluid can flow and a non-thermal plasma generator. The non-thermal plasma generator activates the fluid. In one embodiment the scrubbing device is a mitt. In another embodiment the scrubbing device is a glove.

20 Claims, 9 Drawing Sheets

Related U.S. Application Data

(60) Provisional application No. 62/197,614, filed on Jul. 28, 2015.

(51) Int. Cl.
| | |
|---|---|
| *A47L 13/22* | (2006.01) |
| *A61L 2/18* | (2006.01) |
| *C02F 1/46* | (2023.01) |
| *A47L 13/26* | (2006.01) |
| *C02F 1/00* | (2023.01) |
| *H01J 37/32* | (2006.01) |
| *H05H 1/24* | (2006.01) |
| *A61L 2/00* | (2006.01) |
| *C02F 1/461* | (2023.01) |

(52) U.S. Cl.
CPC ............... *A61L 2/18* (2013.01); *A61L 2/186* (2013.01); *C02F 1/008* (2013.01); *C02F 1/4608* (2013.01); *H01J 37/32348* (2013.01); *H01J 37/32559* (2013.01); *H05H 1/2406* (2013.01); *A47L 2601/02* (2013.01); *A47L 2601/03* (2013.01); *A47L 2601/20* (2013.01); *A61L 2/0011* (2013.01); *A61L 2/0088* (2013.01); *A61L 2202/11* (2013.01); *A61L 2202/14* (2013.01); *A61L 2202/16* (2013.01); *A61L 2202/17* (2013.01); *A61L 2202/26* (2013.01); *C02F 2001/46133* (2013.01); *C02F 2201/4618* (2013.01); *C02F 2201/46135* (2013.01); *C02F 2201/46165* (2013.01); *C02F 2201/46175* (2013.01); *C02F 2209/03* (2013.01); *C02F 2209/40* (2013.01); *C02F 2303/04* (2013.01); *C02F 2305/023* (2013.01); *H01J 2237/335* (2013.01)

(58) Field of Classification Search
CPC .... A47L 2601/20; C02F 1/4608; C02F 1/008; C02F 2201/4618; C02F 2303/04; C02F 2209/03; C02F 2001/46133; C02F 2209/40; C02F 2305/023; C02F 2201/46165; H05H 1/2406; H01J 37/32348; H01J 37/32559; H01J 2237/335; A61L 2/18; A61L 2/14; A61L 2/186; A61L 2/0088; A61L 2202/17; A61L 2202/26; A61L 2202/16; A61L 2202/14; A61L 2/0011; A61L 2202/11
See application file for complete search history.

(56) References Cited

U.S. PATENT DOCUMENTS

| | | |
|---|---|---|
| 5,281,315 A | 1/1994 | Krapivina et al. |
| 5,872,359 A | 2/1999 | Stewart et al. |
| 5,876,663 A | 3/1999 | Laroussi |
| 5,920,799 A | 7/1999 | Graves et al. |
| 6,030,506 A | 2/2000 | Bittenson et al. |
| 6,171,625 B1 | 1/2001 | Denvir et al. |
| 6,176,941 B1 | 1/2001 | Jewett et al. |
| 6,387,238 B1 | 5/2002 | Merk et al. |
| 6,543,460 B1 | 4/2003 | Denes et al. |
| 6,706,243 B1 | 3/2004 | Sias et al. |
| 6,723,091 B2 | 4/2004 | Goble et al. |
| 6,875,399 B2 | 4/2005 | McVey |
| 6,911,225 B2 | 6/2005 | Ruan et al. |
| 6,969,487 B1 | 11/2005 | Sias et al. |
| 7,004,356 B1 | 2/2006 | Sayers |
| 7,008,592 B2 | 3/2006 | Sias et al. |
| 7,163,664 B2 | 1/2007 | Paskalov et al. |
| 7,291,314 B2 | 11/2007 | Paskalov et al. |
| 7,326,382 B2 | 2/2008 | Adiga et al. |
| 7,326,383 B2 | 2/2008 | Gunter et al. |
| 7,569,203 B2 | 8/2009 | Fridman et al. |
| 7,608,839 B2 | 10/2009 | Coulombe et al. |
| 7,829,051 B2 | 11/2010 | Fridman et al. |
| 7,989,673 B2 | 8/2011 | Paskalov et al. |
| 3,048,930 A1 | 11/2011 | Bobbert |
| 8,354,057 B2 | 1/2013 | Heselton et al. |
| 8,383,036 B2 | 2/2013 | Sloan et al. |
| 8,388,618 B2 | 3/2013 | Fridman et al. |
| 9,339,572 B2 | 5/2016 | Tsai et al. |
| 9,550,007 B2 | 1/2017 | Tsai et al. |
| 9,662,412 B2 | 5/2017 | Ferrell et al. |
| 11,123,446 B2 * | 9/2021 | Louis ................ A47L 13/26 |
| 2003/0132100 A1 | 7/2003 | Crowe et al. |
| 2004/0120844 A1 | 6/2004 | Tribelsky et al. |
| 2004/0216845 A1 | 11/2004 | Golkowski |
| 2006/0189976 A1 | 8/2006 | Karni et al. |
| 2006/0223729 A1 | 10/2006 | Hamblin et al. |
| 2006/0229225 A1 | 10/2006 | Martin et al. |
| 2007/0202315 A1 | 8/2007 | Duffield et al. |
| 2007/0251953 A1 | 11/2007 | Criswell et al. |
| 2008/0118734 A1 | 5/2008 | Goodwin et al. |
| 2009/0041617 A1 | 2/2009 | Lee |
| 2009/0054896 A1 | 2/2009 | Fridman et al. |
| 2009/0175956 A1 | 7/2009 | Buschmann et al. |
| 2010/0145253 A1 | 6/2010 | Gutsol et al. |
| 2010/0168499 A1 | 7/2010 | Gutsol et al. |
| 2010/0196505 A1 | 8/2010 | Kaiser et al. |
| 2010/0209293 A1 | 8/2010 | Ikawa et al. |
| 2010/0280513 A1 | 11/2010 | Juergen et al. |
| 2010/0296977 A1 | 11/2010 | Hancock |
| 2011/0112528 A1 | 5/2011 | Stieber et al. |
| 2011/0171188 A1 | 7/2011 | Morfill et al. |
| 2011/0251604 A1 | 10/2011 | Staack et al. |
| 2012/0039747 A1 | 2/2012 | Morfill et al. |
| 2012/0042419 A1 | 2/2012 | Wilson et al. |
| 2012/0100037 A1 | 4/2012 | Shannon et al. |
| 2012/0305787 A1 | 12/2012 | Henson |
| 2012/0315684 A1 | 12/2012 | Hayashi et al. |
| 2014/0003998 A1 | 1/2014 | Franklin et al. |
| 2014/0100277 A1 | 4/2014 | Gray et al. |
| 2014/0271354 A1 | 9/2014 | Tsai et al. |
| 2014/0322096 A1 | 10/2014 | Pelfrey et al. |
| 2015/0038584 A1 | 2/2015 | Fridman et al. |
| 2015/0306258 A1 | 10/2015 | Ferrell et al. |
| 2016/0051713 A1 | 2/2016 | Robert |
| 2016/0166607 A1 | 6/2016 | Roe et al. |
| 2016/0367712 A1 | 12/2016 | Robert |

FOREIGN PATENT DOCUMENTS

| | | |
|---|---|---|
| WO | 02059046 A2 | 8/2002 |
| WO | 2005123891 A2 | 12/2005 |
| WO | 2006076334 A1 | 7/2006 |
| WO | 2006116252 A2 | 11/2006 |
| WO | 2007048806 A1 | 5/2007 |
| WO | 2007063987 A1 | 6/2007 |
| WO | 2010009103 A2 | 1/2010 |
| WO | 2010022160 A2 | 2/2010 |
| WO | 2010085513 A1 | 7/2010 |
| WO | 2010107722 A1 | 9/2010 |
| WO | 2010107741 A1 | 9/2010 |
| WO | 2010107744 A1 | 9/2010 |
| WO | 2010107745 A1 | 9/2010 |
| WO | 2010107746 A1 | 9/2010 |
| WO | 2012018891 A2 | 2/2012 |
| WO | 2012112042 A1 | 8/2012 |
| WO | 2014145570 A1 | 9/2014 |

OTHER PUBLICATIONS

International Search Report and Written Opinion from International Application No. PCT/US2014/030361, dated Jul. 16, 2014.

International Search Report and Written Opinion from PCT/US2016/044160, dated Jan. 19, 2017.

Office Action from European Application No. 14724869.4 dated Oct. 31, 2016.

Alekseev et al., "Nonthermal Dielectric Barrier Discharge (DBD)

(56) References Cited

OTHER PUBLICATIONS

Plasma Suppresses Herpes Simplex Virus Type 1 (HSV-1) Replication in Corneal Epithelium", TVST, 2014, vol. 3, No. 2, Article 2, pp. 1-14.
Alhabshan et al., "Effects of In-vivo Application of Cold Atmospheric Plasma on Corneal Wound Healing in New Zealand White Rabbits", International Journal of Ophthalmic Pathology, 2013, 2:3, pp. 1-5.
Andrade et al., A new, versatile, direct-current helium atmospheric-pressure glow discharge. Journal of Analytical Atomic Spectrometry, 2006. 21(11): p. 1175-1184.
Blajan, et al., Emission spectroscopy of pulsed powered microplasma for surface treatment of PEN film. Industry Applications, IEEE Transactions on, 2011. 47(3): p. 1100-1108.
Bruggeman et al., Non-thermal plasmas in and in contact with liquids. Journal of Physics D: Applied Physics, 2009. 42 (5): p. 053001.
Brun et al., "Disinfection of Ocular Cells and Tissues by Atmospheric-Pressure Cold Plasma", PLoS ONE, Mar. 2012, vol. 7, Issue 3, e33245, pp. 1-13.
Burlica et al. "Formation of H2 and H2O2 in a Water-Spray Gliding Arc Nonthermal Plasma Reactor", Industrial & Engineering Chemistry Research, vol. 49, No. 14, Jun. 24, 2010.
Cabiscol et al., Oxidative stress in bacteria and protein damage by reactive oxygen species. International Microbiology, 2010. 3(1): p. 3-8.
Critzer et al., "Atmospheric Plasma Inactivation of Foodborne Pathogens on Fresh Produce Surfaces", Journal of Food Protection, vol. 70, No. 10, 2007, pp. 2290-2296.
Danil et al., Cold Plasma Inactivation of Bacillus Cereus and *Bacilus antracis* (Anthrax) Spores, IEEE Service Center, Piscataway NJ, US vol. 38, No. 8, Aug. 1, 2010, pp. 1878-1884.
Daifas et al., Effect of ethanol vapor on growth and toxin production by Clostridium botulinum in a high moisture bakery product. Journal of food safety, 2000 20(2): p. 111-125.
Ermolaeva et al., "Bactericidal effects of non-thermal argon plasma . . . ", J. Med. Microbiol., Sep. 2010, http://jmm.sgmjournals.org/content/60/1/75.full.
Escobar-Cortes et al., "Proteases and sonication specifically remove the exosporium layer . . . ", J. Microbiol. Methods, Jan. 2013.
Gaunt et al., Bactericidal action of the reactive species produced by gas-discharge nonthermal plasma at atmospheric pressure: a review. Plasma Science, IEEE Transactions on, 2006. 34(4): p. 1257-1269.
Gil et al., Fresh-cut product sanitation and wash water disinfection: problems and solutions. International journal of food microbiology, 2009. 134(1): p. 37-45.
Hayashi et al., Sterilization of medical equipment using radicals produced by oxygen/water vapor RF plasma. Japanese journal of applied physics, 2006. 45(10S): p. 8358.
Huang, "Non-thermal Plasma Inactivation of Bacillus Amyloliquefaciens Spores", Master's Thesis, Univ. of Tennessee, 2011, http://www.trace.tennessee.edu/utk.sub.-gradthes/980.
Joshi, S.G., et al., Nonthermal dielectric-barrier discharge plasma-induced inactivation involves oxidative DNA damage and membrane lipid peroxidation in *Escherichia coli*. Antimicrobial agents and chemotherapy, 2011. 55(3): p. 1053-1062.
Klampfl, T.G., et al., Cold atmospheric air plasma sterilization against spores and other microorganisms of clinical Interest. Applied and Environmental Microbiology, 2012. 78(15): p. 5077-5082.
Klimpel, Clostridium Difficle Test Exposure to BIT Plasma, Plasma Clostridium Difficile Killing Trials, 2009 (5 pages).
Laroussi, M. and F. Leipold, Evaluation of the roles of reactive species, heat, and UV radiation in the inactivation of bacterial cells by air plasmas at atmospheric pressure. International Journal of Mass Spectrometry, 2004. 233(1): p. 81-86.
Lawley et al., "Proteomic and Genomic Characterization of Highly Infectious . . . ", J. Bacteriol. 2009, vol. 191, No. 17, pp. 5377-5386, Jun. 2009, http://jb.asm.org/content/191/1715377.
Lawley et al., "Use of Purified Clostridium difficile Spores . . . ", Appl. Environ. Microbiol., pp. 6895-6900, Aug. 2010.
Lerouge et al., Plasma sterilization: a review of parameters, mechanisms, and limitations. Plasmas and Polymers, 2001. 6(3): p. 175-188.
Lukes et al., Aqueous-phase chemistry and bactericidal effects from an air discharge plasma in contact with water: evidence for the formation of peroxynitrite through a pseudo-second-order post-discharge reaction of H2O2 and HNO2. Plasma Sources Science and Technology, 2014. 23(1): p. 015019.
Machala et al., Formation of ROS and RNS in Water Electro-Sprayed through Transient Spark Discharge in Air and their Bactericidal Effects. Plasma Processes and Polymers, 2013. 10(7): p. 649-659.
Matthes et al., Antimicrobial Efficacy of Two Surface Barrier Discharges with Air Plasma against In Vitro Biofilms. PloS one, 2013. 8(7): p. e70462.
Misra et al., Nonthermal plasma inactivation of food-borne pathogens. Food Engineering Reviews, 2011. 3(3-4): p. 159-170.
Oehmigen et al., "The Role of Acidification for Antimicrobial . . . ", Wiley InterScience, Plasma Process, and Polym. 2010, 7, pp. 250-257, 2010.
Niemira, Cold Plasma Inactivates *Salmonella stanley* and *Escherichia coli* O157:h7 Inoculated on Golden Delicious Apples, Journal of Food Protection, vol. 71, No. 7, 2008, pp. 1357-1365.
Niemira, Cold Plasma Decontamination of Foods. Annual Review of Food Science and Technology, 2012. 3: p. 125-142.
Pankaj et al., Applications of cold plasma technology in food packaging. Trends in Food Science & Technology, 2014. 35(1): p. 5-17.
Pappas, Status and potential of atmospheric plasma processing of materials. Journal of Vacuum Science & Technology A, 2011. 29(2): p. 020801.
Paredes-Sabja, et al., "Adherence of Clostridium difficile spores to Caco-2 cells in culture", J. Med. Microbiol., pp. 1208-1218, 2012.
Park et al., "Reactive nitrogen species produced in water by non-equilibrium plasma increase plant growth rate and nutritional yield", Current Applied Physics 13 (2013), pp. 519-529.
Pei et al., "Inactivation of a 25.5 . . . Enterococcus faecalis biofilm . . . ", J. Phys. D: Appl. Phys., http://www.stacks.iop.org/JPhysD/45/165205, Apr. 2012.
Sera et al., "Germination of Chenopodium Album in Response to Microwave Plasma Treatment", Plasma Science and Technology, vol. 10, No. 4, Aug. 2008, pp. 506-511.EA.
Sosnin et al., The effects of UV irradiation and gas plasma treatment on living mammalian cells and bacteria: a comparative approach Plasma Science, IEEE Transactions on, 2004. 32(4): p. 1544-1550.
Tolls et al., Surface Layers of Clostridium difficile Endospores, J. Bacteriol. 2011, vol. 193, No. 23, pp. 6461-6470, 2011.
Traylor et al., "Long-term antibacterial efficacy of air plasma-activated water", J. Phys. D: Appl. Phys., Nov. 2011, http://www.stacks.iop.org/JPhysD/44/472001.
Tsai et al. Rapid Inactivation of Bacterial Spores Using Plasma Activated Water:Development, Species Identification and Sporicidal Mechanism, 22nd Internation Symposium on Plasma Chemistry, Jul. 5, 2015, pp. 1-4.
Utku et al., Nonequilibrium Plasma-Activated Antimicrobial Solutions are Broad-Spectrum and Retain Their Efficacies for Extended Period of Time, Plasma Processes and Polymers, vol. 10, No. 6, Apr. 12, 2013, pp. 544-555.
Venezia, et al., "Lethal Activity of Nonthermal Plasma . . . ", Univ. of Chicago Press, Infection Control and Hospital Epidemiology, vol. 29, No. 5, May 2008, http://www.jstororg/stable/10.1086/588003.
Von Woedtke et al., Plasma-liquid interactions: chemistry and antimicrobial effects, in Plasma for Bio-Decontamination, Medicine and Food Security. 2012, Springer, p. 67-78.
Zhu et al., A de non-thermal atmospheric-pressure plasma microjet. Plasma Sources Science and Technology, 2012. 21(3): p. 034018.

\* cited by examiner

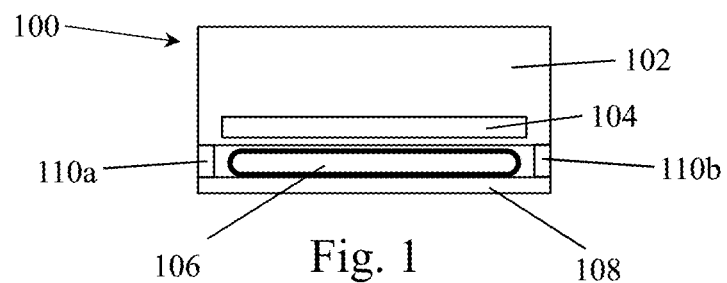
Fig. 1
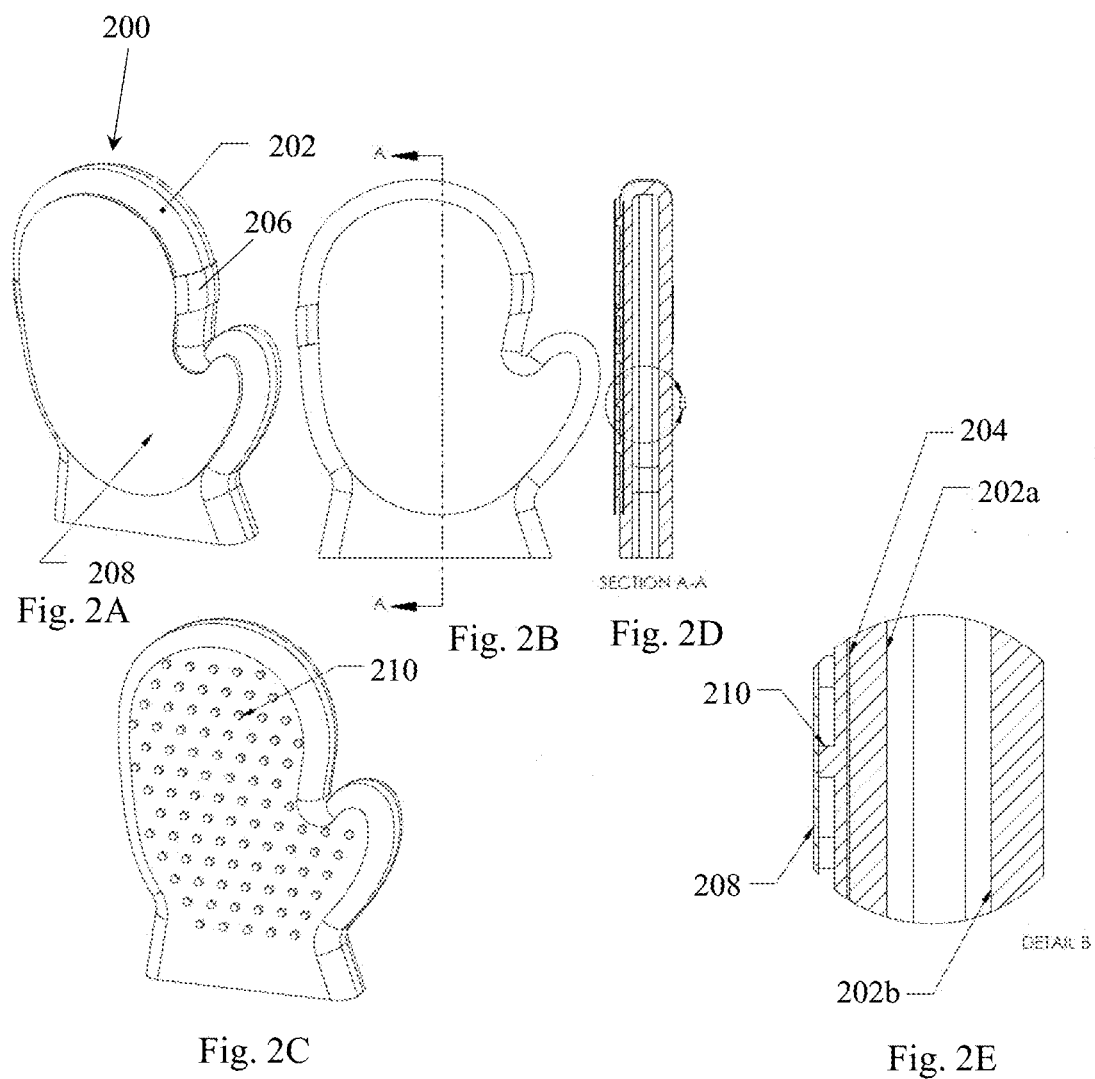
Fig. 2A  Fig. 2B  Fig. 2D
Fig. 2C  Fig. 2E

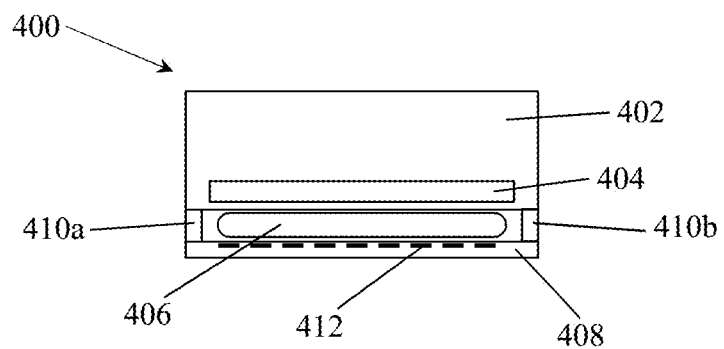
Fig. 4
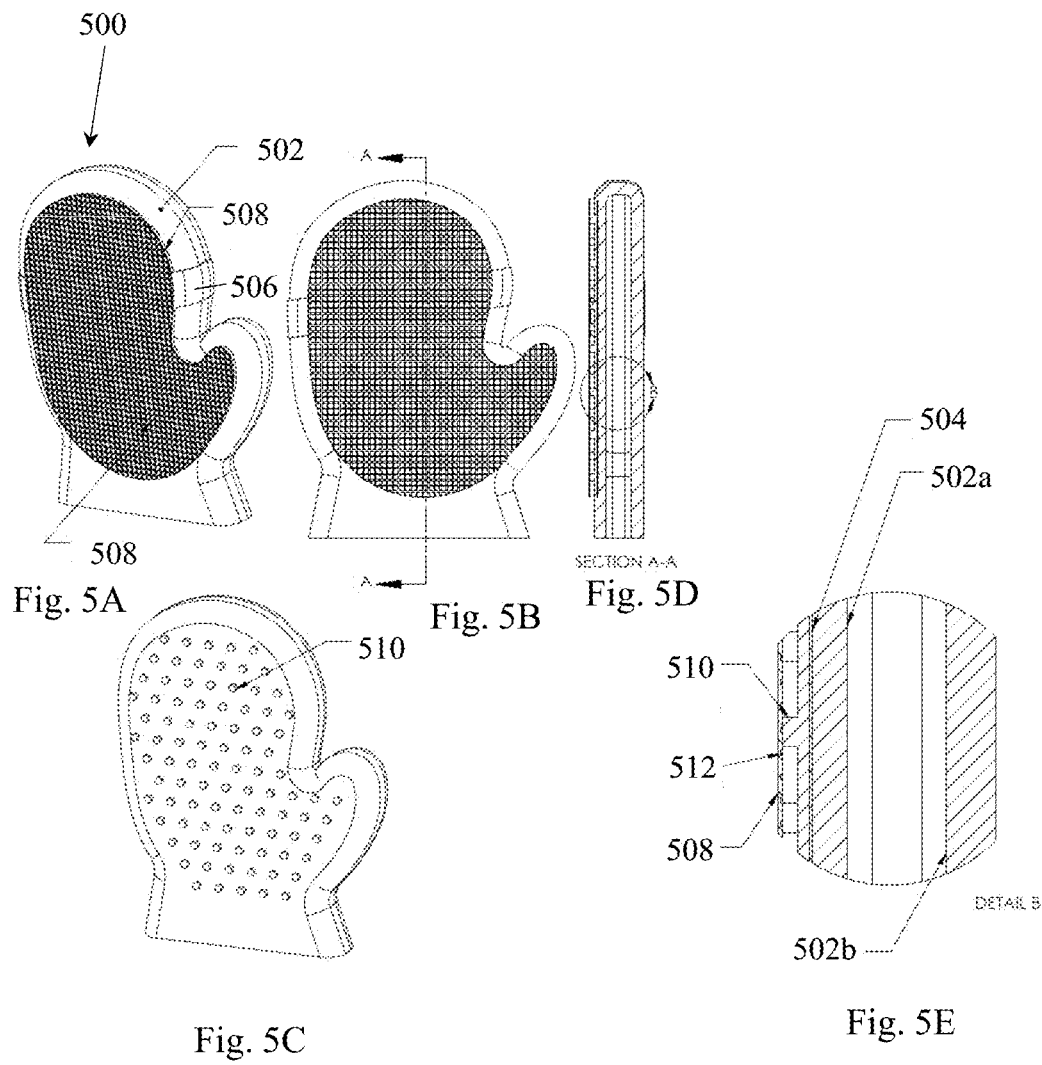
Fig. 5A  Fig. 5B  Fig. 5D
Fig. 5C  Fig. 5E

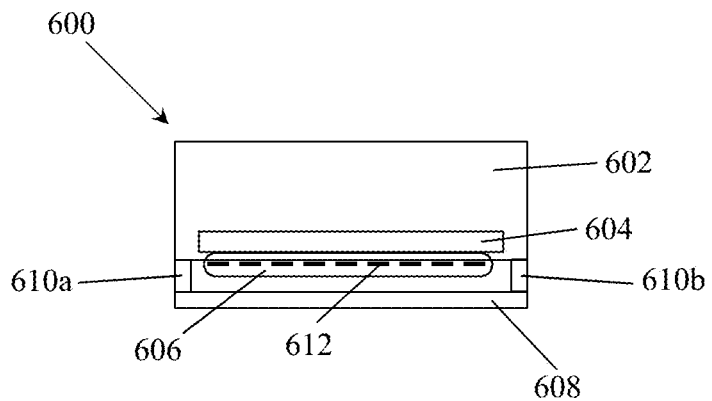
Fig. 6
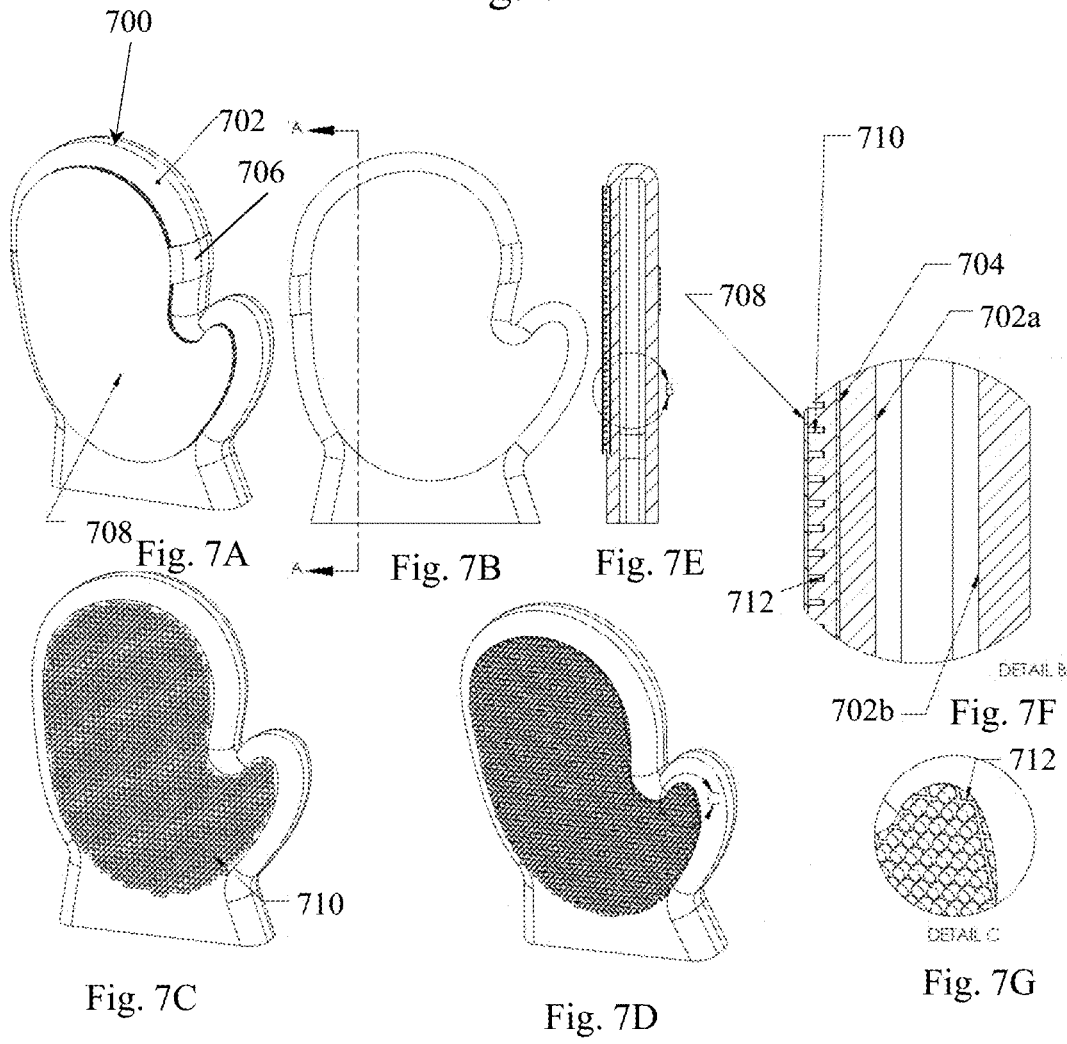
Fig. 7A  Fig. 7B  Fig. 7E
Fig. 7C  Fig. 7D  Fig. 7F
Fig. 7G

SCRUBBING DEVICE FOR CLEANING, SANITIZING OR DISINFECTING

RELATED APPLICATIONS

This application is a continuation of U.S. patent application Ser. No. 15/747,478, entitled Scrubbing Device for Cleaning, Sanitizing or Disinfecting, which was filed on Jan. 25, 2018 and which will issue as U.S. Pat. No. 11,123,446 on Sep. 21, 2021, and which is incorporated herein by reference in its entirety. This non-provisional utility patent application also claims priority to and the benefits of PCT application No. PCT/US2016/044160, which was filed on Jul. 27, 2016 and entitled Scrubbing Device for Cleaning, Sanitizing or Disinfecting and priority to and the benefits of U.S. Provisional Patent Application Ser. No. 62/197,614 filed on Jul. 28, 2015 and entitled PLASMA STERILIZATION OF TISSUE, both of which are incorporated herein by reference in their entirety.

TECHNICAL FIELD

The present invention relates generally to cleaning, sanitizing or disinfecting scrubbing devices and more particularly to cleaning, sanitizing or disinfecting scrubbing devices using non-thermal plasma activated fluids.

BACKGROUND OF THE INVENTION

People receiving medical care can acquire serious infections called healthcare-associated infections (HAIs). Common HAIs are caused by bacteria, germs, and the like. While most types of HAIs are declining, one caused by the germ *Clostridium difficile*, "*C. difficile*" remains at historically high levels. *C. difficile* is linked to 14,000 American deaths each year. Especially at risk are older adults who take antibiotics and receive long term medical care.

*C. difficile* is an anaerobic, Gram positive bacterium. Normally fastidious in its vegetative state, it is capable of sporulating when environmental conditions no longer support its continued growth. The capacity to form spores enables the organism to persist in the environment (e.g., in soil and on dry surfaces and under oxygen pressure) for extended periods of time.

Current methods of killing or deactivating *C. difficile* include applying bleach, liquid solutions containing hydrogen peroxide, and other biocidal compounds for a period of time longer than 3 minutes, and/or ultraviolet radiation (UV) to *C. difficile* for a period of time longer than 10 minutes.

TOMI Environmental Solutions published a paper titled "*Clostridium difficile* Test Exposure to BIT® Plasma" that purported to demonstrate killing *C. difficile* on stainless steel coupons by exposing the *C. difficile* to BIT® Plasma for five minutes followed by a 5-minute dwell period in a closed chamber. The paper states that the BIT® Plasma test chamber was designed to generate an indirect spray and approximate the fogging process when the commercial SteraMist™ Fogger System is used in a hospital room. The paper also states that "the height average concentration of hydrogen peroxide reaches just above 300 ppm at the beginning of the dwell period and falls slowly until the coupons are removed," and that the results "are the first direct evidence of spore killing by aerosolized activated hydrogen peroxide." This system appears to require a total 10-minute treatment time (5-minute exposure time plus 5-minute dwell time).

It is believed that the SteraMist™ Fogger System is disclosed in U.S. Pat. Nos. 6,969,487 and 7,008,592. These patents disclose activating a cleaning fluid that preferably comprises a source of hydroxyl ions ($OH^-$) for subsequent activation, such as hydrogen peroxide ($H_2O_2$). The patents also disclose using arc plasma, e.g., a 10.5 kilovolt AC arc. Although the patents state that the cleaning fluid is a fluid that contains an activable species, it appears that the '592 teaches that water is not an activable species. For example, the '592 patent discloses that "the specimen contacted by the 0 percent hydrogen peroxide [i.e. "activated" water vapor only] mist showed significant growth of the bacteria culture." See col. 9, lines 45-55. In addition, the AC arc illustrated in the TOMI system is a relatively higher temperature process that shortens the life of short-lived species that are believed to be needed to kill spores.

One of the reasons it is very difficult to kill or deactivate dry spores is due to their tendency to aggregate and form multilayered structures. In addition, the dry spores adhere to surfaces and skin very strongly, making it very difficult to physically remove them.

The currently available methods for disinfecting and/or inactivating bacteria and spores are time intensive, such as treating with bleach for more than 5 minutes. Thus, HAIs remain a very serious problem and approved methods require up to 5 minutes of treatment time.

SUMMARY

Exemplary methods and systems for scrubbing, cleaning, sanitizing or disinfecting are disclosed herein. An exemplary device for cleaning, sanitizing or disinfecting includes a body that has a first surface for scrubbing a surface to be cleaned a plasma generator for generating plasma and a fluid. The non-thermal plasma generator activates the fluid and the plasma activated fluid is applied to the surface to be cleaned. The first surface is used to scrub the surface to be cleaned.

Another exemplary sanitizing, disinfecting or cleaning device includes a reservoir for holding a water-based fluid and a fluid delivery element for expelling the water-based fluid in the form of a mist, a spray or a vapor. The fluid delivery element is connected to the reservoir by a passage through which the fluid can flow. A plasma generator having at least one electrode surrounded by a dielectric barrier and a scrubbing material are also included. A high voltage source is applied to the at least one electrode, non-thermal plasma is produced in gas near the at least one electrode to activate the water-based fluid; and the scrubbing material is used to scrub a surface.

Another exemplary cleaning, disinfecting or sanitizing device includes a body, a non-thermal plasma generating device secured to the body, a fluid reservoir, and a scrubbing material. The plasma generating device generates plasma to activate the fluid.

BRIEF DESCRIPTION OF THE DRAWINGS

These and other features and advantages of the present invention will become better understood with regard to the following description and accompanying drawings in which:

FIG. 1 is a schematic view of an exemplary embodiment of a cleaning, sanitizing, or disinfecting scrubbing device which consists of a non-thermal plasma generator and a moistened scrubbing material, in which the fluid is activated by a volumetric plasma created between the plasma generator and the scrubbing material;

FIGS. 2A, B and C are isometric views of the cleaning, sanitizing, or disinfecting scrubbing mitt and FIG. 2D is a cross-section of the mitt and FIG. 2E is a cross sectional detail of the mitt;

FIG. 4 is a schematic view of another exemplary embodiment of a cleaning, sanitizing, or disinfecting scrubbing device which consists of a non-thermal plasma generator and a moistened scrubbing material, in which the fluid is activated by a volumetric plasma created between the plasma generator and the grounded electrodes embedded in the wipe;

FIGS. 5A, B and C are isometric views of the cleaning, sanitizing, or disinfecting scrubbing mitt and FIG. 5D is a cross-section of the mitt and FIG. 5E is a cross sectional detail of the mitt;

FIG. 6 is a schematic view of yet another exemplary embodiment of a cleaning, sanitizing, or disinfecting scrubbing device which consists of a non-thermal plasma generator and a moistened scrubbing material, in which the fluid is activated by a volumetric or surface plasma created between the plasma generator and the grounded electrodes in the vicinity of the plasma generator;

FIGS. 7A, 7B, 7C and 7D are isometric views of an exemplary cleaning, sanitizing, or disinfecting scrubbing mitt and FIG. 7E is a cross-section of the mitt and FIG. 7F is a cross-sectional detail of the mitt, and FIG. 7G is an enlarged detail of a portion of the mitt;

DETAILED DESCRIPTION

Figure 3:
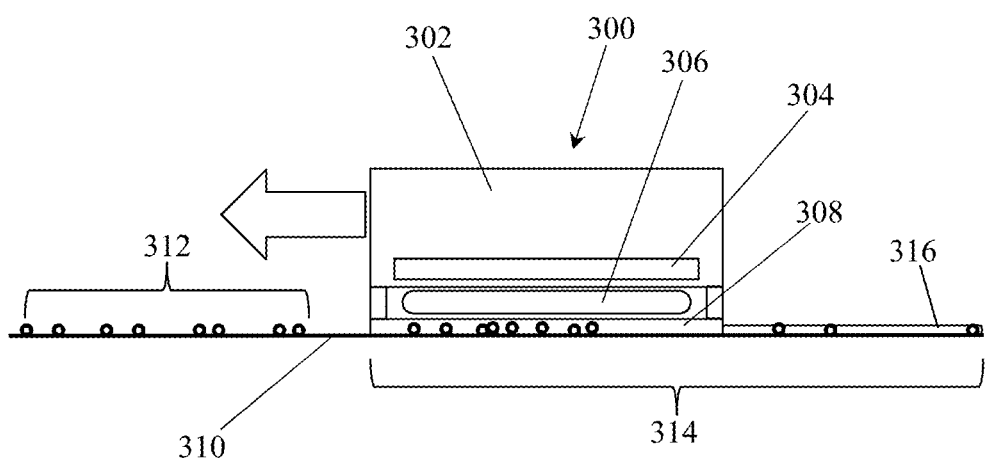
FIG. 3 is a schematic view of a method of using a plasma-enhanced cleaning, sanitizing, or disinfecting scrubbing device.

Plasmas, or ionized gases, have one or more free electrons that are not bound to an atom or molecule. Plasmas may be generated using a variety of gases including, air, nitrogen, noble gases (He, Ar, Xe, Kr, etc), oxygen, carbon dioxide and mixtures thereof under an applied electric field. In addition, non-thermal plasmas provide high concentrations of energetic and chemically active species. They can operate far from thermodynamic equilibrium where the temperature of free electrons in the plasma is significantly higher than neutral atoms, ions and molecules. Such plasmas have high concentrations of active species and yet remain at a temperature that is substantially the same as room temperature. The energy from the free electrons may be transferred to additional plasma components initiating additional ionization, excitation and/or dissociation processes. Fluid that is contacted with plasma may become "activated" and is referred to herein as plasma activated fluid.

In some embodiments, plasmas may contain superoxide anions $[O_2.^-]$, which react with $H^+$ in acidic media to form hydroperoxy radicals, HOO.$^\cdot$ $[O_2.^-]+[H^+]\rightarrow[HOO.]$. Other radical species may include OH. and NO. in gaseous or aqueous phase with the presence of air or gas. Properly treating water with non-thermal air plasma results in plasma activated water that may contain concentrations of one or more of atomic oxygen, ozone, $H_2O_2$, nitrates, nitrites, peroxynitrite, peroxynitrous acid, hydroxyl radicals and other active species.

Activating water with plasma to obtain plasma activated water is shown and described in U.S. Non-Provisional application Ser. No. 13/829,877 titled Sanitization Station Using Plasma Activated Fluid, filed on Mar. 14, 2013, which claims priority to U.S. Provisional Application Ser. No. 61/621,078 also titled Sanitization Station Using Plasma Activated Fluid, filed on Apr. 6, 2012 and U.S. Pat. No. 9,339,572 titled Methods of Making Solutions to Kill or Deactivate Spores Microorganisms, Bacteria and Fungus, filed on Mar. 15, 2013 and U.S. Non-Provisional application Ser. No. 13/842,574 titled Methods of Making Solutions to Kill or Deactivate Spores Microorganisms, Bacteria and Fungus, filed on Mar. 15, 2013 and U.S. Provisional Application Ser. No. 61/710,263 also titled Solutions and Methods of Making Solutions to Kill or Deactivate Spores, Microorganisms, Bacteria and Fungus, filed on Oct. 5, 2012, all of which are incorporated by reference herein in their entirety. Several other patents and applications disclose activating fluid, such as PCT Application Nos. WO 02/059046, titled Method of Activation of Chemically Pure and Potable Water and filed on Jan. 25, 2002; WO 2007/048806, titled Method for the Preparation of Biocidal Activated Water Solutions and filed Oct. 25, 2006; WO 2012/018891, which is titled Materials for Disinfection Produced by Non-Thermal Plasma and was filed on Aug. 3, 2011; and U.S. Pat. No. 7,291,314, titled Activated Water Apparatus and Methods and filed Dec. 20, 2001, and are incorporated herein by reference in their entirety. These methods may be used to activate other formulations which are typically water based formulations.

Embodiments of the present invention provide a novel combination of devices that provide effective use of fluids for cleaning, sanitizing or disinfecting along with a scrubbing material. FIG. 1 is a schematic view of an exemplary embodiment of a device 100 for cleaning, sanitizing or disinfecting a surface (not shown) by wiping and treating the surface with a material 108 that contacts the surface to be cleaned with a scrubbing material and activated fluid.

The device 100 generally includes a housing 102. The housing 102 includes a cavity for receiving a thumb and additional cavities for receiving the fingers of a hand. In some embodiments the housing 102 has a sock shape that covers the thumb and fingers of a hand. In some embodiments, the housing has a glove shape, having individual cavities for the thumb and fingers. Thus, in the following embodiments, the term "housing" may refer also to a sock, a sleeve, a glove, or the like. In addition, in some embodiments, one or more cavities for the fingers or thumb may be open and expose all or part of the fingers and thumbs. In some embodiments, the housing 102 can be attached to a handheld device or any other devices to achieve cleaning, sanitizing, and disinfecting.

In some embodiments the housing 102 is made from a flexible material such as, for example, cloth, fabric, rubber, silicone or the like. In some embodiments the interior surface of the housing 102 is made from a different material than the exterior surface. For example, the exterior surface may be made of a water resilient material, such as, for example rubber to prevent fluid from permeating the housing 102, while the other surface may be made of a soft material, such as cotton for comfort against a user's hand. In some embodiments, both the exterior and interior surface may be made of a soft material and a water resilient material may be located between the surfaces.

The device 100 further generally includes a non-thermal plasma generator 104. In some embodiments, the plasma generator 104 is embedded in the housing 102. Plasma generator 104 generates plasma 106. The plasma generator 104 may be a dielectric barrier discharge (DBD), corona discharge, plasma jet, micro plasma, or glow discharge plasma generator. The plasma generator 106 may be powered by a DC, pulsed DC, pulsed AC, AC sinusoidal, RF or microwave power supply. The power supply can have various pulse durations and may be, for example, a microsecond power supply, a nanosecond power supply, or the like. The power supply (not shown) may be a battery, integrated with the housing 102, and may be a part of the device 100. The power supply can also be separate from the housing 102 and mounted remotely, on for example, a cart (not shown) or carried in, for example, a back pack (not shown) and device 100 may be tethered to the power supply.

In some embodiments plasma 106 is generated in ambient air in proximity to the plasma generator 104. In some embodiments the plasma generator 104 includes a gas supply, which may be included in the housing 102 or located remotely, on for example on a cart (not shown), on a back pack (not shown) or the like. In addition to ambient air, suitable gases for plasma generation may include noble gases, such as helium or argon, molecular gases, such as oxygen, nitrogen, air, gases carrying evaporated liquids, or any mixture thereof.

In this exemplary embodiment, device 100 also includes a scrubbing material, which in this exemplary embodiment is a wipe 108, however the scrubbing material could be any type of material suitable for wiping or rubbing. Wipe 108 may be, for example a non-woven wipe. In some embodiments, the wipe is pre-moistened and the fluid is activated by plasma while on the wipe 108. In some embodiments, the wipe 108 is moistened with fluid after the fluid is activated by plasma. If the wipe 108 is moistened with fluid after the fluid is activated, the fluid may be carried in a container or cavity in or on the housing 102 or separate from the housing 102 on for example, a cart (not shown), a back pack (not shown) or the like. The term scrubbing material as used herein is any suitable material that may be used to scrub or wipe a surface to be cleaned. Although exemplary embodiments use a wipe as the scrubbing material, the term scrubbing material is broader than a wipe. In some embodiments, the scrubbing material is permanent, in some embodiments the scrubbing material is detachable and removable.

In some embodiments, the wipe 108 is moistened (or pre-moistened) with water, for example, tap water, distilled water, saline, deionized water, buffered salt solution or reverse osmosis water. In further embodiments the water includes an additive. In some embodiments the additive is an alcohol, for example, ethanol or isopropyl alcohol or a combination thereof. In some embodiments the additive is hydrogen peroxide. In some embodiments the additive is a nitrite such as sodium nitrite or nitrous acid. In some embodiments the additive is a quaternary ammonium compound. In some embodiments the additive is a bio-active oil, such as, for example, coconut oil, grape seed oil or olive oil. In some embodiments the additive is an acid, for example, acetic acid, citric acid, nitrous acid or hydrochloric acid. In some embodiments that additive is an enzyme, for example, superoxide dismutase, nitrate reductase. In some embodiments the additive is a combination of one or more of the above additives. In other embodiments the wipe is moistened with any of (or a combination of) the above additives with or without water. And in yet further embodiments a dry wipe is instead subjected to a plasma activated mist, vapor or spray including water and/or any of the above additives to produce a sufficient volume of plasma activated fluid in the wipe 108.

The wipe 108 provides both mechanical removal of microbes, through physical contact with the contaminated surface, and deactivation of the microbes by the plasma activated fluid. In some embodiments the wipe 108 is a disposable wipe. In some embodiments, wipe 108 is reusable. The wipe 108 may made of a soft absorbent material such as a non-woven, a cloth, foamed polymer, or wood fiber or pulp. In some embodiments the wipe 108 includes an abrasive material, such as for example steel wool, or the like, and in some embodiments, wipe material 108 includes a rubber material, such as, for example, one or more squeegees, projections, or the like. In some embodiments the wipe 108 may include a mix of one or more of an abrasive material, an absorbent material and a rubber material.

The wipe 108 may be attached to the housing 102 by any means, such as, for example, with a strap, a fastener, for example a hook and loop fastener or the like. In some embodiments, the wipe 108 fits over and encases at least a portion of the housing 102. The device 100 may include spacer posts, such as spacer posts 110a and 110b on the bottom side of the housing 102, to create an open area for the plasma 106.

FIGS. 2A-2E depict several views of an exemplary scrubbing device 200, based on the concept shown in FIG. 1, as a mitt. The device 200 includes a mitt 202, which may be of any of the types described above. The mitt 202 includes an inner palm-side surface 202a and an inner back-of-hand-side surface 202b. The device 200 further includes wipe 208, which may be of any of the types of scrubbing materials described above and moistened (or pre-moistened) with any of the fluids described above. The wipe 208 is fastened to the mitt 202 via strap 206. In some embodiments, wipe 208 is fastened to mitt 202 by other means, such as, for example, hook and loop fasteners, one or more clamps, projections or the like. In some embodiments, the wipe 208 is spaced apart from the mitt 202 by an array of spacer posts 210 to space the wipe 208 away from electrode 204. The device 200 further includes an electrode 204 for plasma generation (the wipe 208 or surface being cleaned serves as a ground or floating electrode) and plasma is generated between bottom surface of the mitt 202 and the outside surface of wipe 208 when a sufficiently high voltage is applied to the electrode 204. In some embodiments, the mitt 202 includes a dielectric material at lease in the area surrounding the embedded electrode 204. In some embodiments, the electrode 204 is made from a flexible conductive material embedded in the mitt 202, and may contain copper, silver, aluminum, gold, carbon nanotubes, carbon nanowires or the like, or mixtures of one or more of these conductive materials.

FIG. 3 shows the exemplary non-thermal plasma-assisted cleaning, sanitizing, or disinfecting scrubbing device 300 in use. The device 300 may be of any type described herein. In the exemplary illustration, the device 300 is moving from right to left as depicted by the arrow. The scrubbing device 300 includes a housing 302, plasma generator 304 that creates a plasma 306, and a pre-moistened wipe 308. The plasma wiping device 300 is actively cleaning a surface 310 that includes microbes 312.

As depicted in FIG. 3, when the plasma-enhanced scrubbing device 300 moves across the surface 310, it picks up most of the microbes and kills or deactivates the microbes. In some embodiments, the device may leave behind a few deactivated microbes 314, however, the microbes 314 are dead or deactivated. In some embodiments, the device 300 also leaves a plasma activated liquid film 316 on the surface 310 that continues to disinfect the surface 310 even after the device 300 has passed.

FIG. 4 is a schematic view of another exemplary embodiment of a device 400 for cleaning, sanitizing or disinfecting a surface (not shown) by wiping it with an activated fluid. Similar to the device 100 described above, the device 400 includes a housing 402, plasma generator 404 that generates a plasma 406, a wipe 408 and spacer posts, such as spacer posts 410a and 410b. Each these aspects of the device 400 may vary as described above for similar aspects of the device 100.

In the exemplary device 400, the wipe 408 includes an embedded conductive mesh 412. The embedded conductive mesh 412 serves as a ground electrode or a floating electrode for the plasma generator 404. The embedded conductive mesh 412 may contain copper, silver, aluminum, gold, carbon nanotubes, carbon nanowires or the like, or mixtures of one or more of these conductive materials. In some embodiments, the wipe may be made of a conductive polymer or conductive polymer foam and no separate conductive mesh would be required. The conductive mesh 412 may be any suitable thickness and the spacing between the wires may be uniform or varied whereas the wire diameter can also be varied. In some embodiments the conductive mesh 412 can be replaced by any of perforated conductive materials. In some embodiments the conductive mesh 412 is coated by a dielectric material, such as Teflon or glass. In some embodiments, the conductive mesh is a steel wool, or brillo pad.

FIGS. 5A-5E depict several views of an exemplary scrubbing device 500, based on the concept shown in FIG. 4, as a mitt. The device 500 includes a mitt 502, which may include one or more elements of any of the devices disclosed herein. The mitt 502 includes an inner palm-side surface 502a and an inner back-of-hand-side surface 502b. The device 500 further includes wipe 508, which may be of any of the types described herein and moistened with any of the liquids described herein. The wipe 508 is fastened to the mitt 502 via strap 506, however may be fastened to the mitt 502 by other means, such as, for example, one or more hook and loop fasteners, one or more projections, one or more clamps, and the like. The wipe 508 is spaced apart from the mitt 502 by an array of spacer posts, such as spacer post 510. The device 500 further includes an electrode 504 for plasma generation and the wipe 508 includes an embedded conductive mesh 512 as a second electrode.

FIG. 6 is a schematic view of another exemplary embodiment of a device 600 for cleaning, sanitizing or disinfecting a surface (not shown) by wiping it with an activated fluid.

Similar to the device 100 described above, the device 600 includes a housing 602, plasma generator 604 that generates plasma 606, a wipe 608 and spacer posts 610a and 610b. In some embodiments, no spacer post 610a are used.

The exemplary device 600 includes a conductive mesh 612 situated between the housing 602 and wipe 608. The conductive mesh 612 serves as a second electrode for the plasma generator 604. The conductive mesh 612 may contain copper, silver, aluminum, gold, carbon nanotubes, carbon nanowires, conductive polymer, or the like, or mixtures of one or more of these conductive materials. The conductive mesh 612 may be any suitable thickness. In some embodiments the conductors of the conductive mesh 612 and the spacer posts (e.g., spacer posts 610a and 610b) are correspondingly spaced such that the spacer posts hold the conductive mesh 612 in place. In some embodiments a gap between the housing 602 and the conductive mesh 612 is required to create volumetric plasma. In some embodiments no gap between the housing 602 and the conductive mesh 612 is required to create surface plasma. In some embodiments the conductive mesh 612 can be replaced by any of perforated conductive materials. In some embodiments the conductive mesh 612 is coated by a dielectric material, such as Teflon or glass.

FIG. 7 depicts several views of an exemplary scrubbing device 700, based on the concept shown in FIG. 6, as a mitt. The device 700 includes a mitt 702, which may be of any of the types described herein. The mitt 702 includes an inner palm-side surface 702a and an inner back-of-hand-side surface 702b. The device 700 further includes wipe 708, which may be of any of the types described herein and moistened or pre-moistened with any of the liquids described herein. The wipe 708 is fastened to the mitt 702 via strap 706. The wipe 708 is spaced apart from the mitt 702 by an array of spacer posts, such as spacer post 710. The device 700 further includes an electrode 704 for plasma generation and a conductive mesh 712 as a second electrode. As seen in detail in FIG. 7F, the array of spacer posts is spaced closely together and in some embodiments, conform to the gaps in the conductive mesh 712 and hold the mesh 712 in place.

Figure 8:
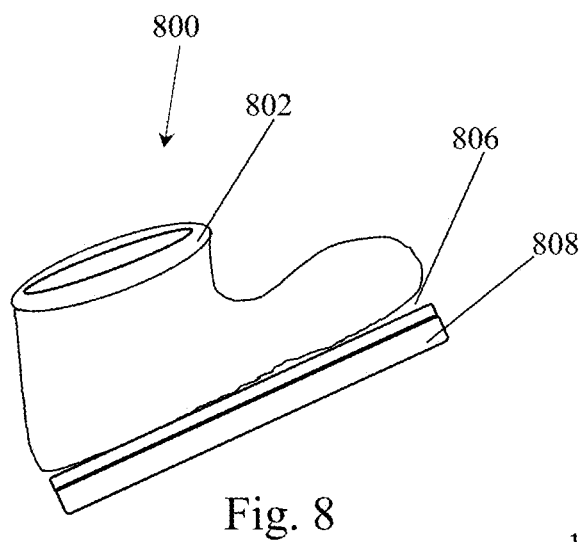
FIG. 8 is a schematic view of an exemplary embodiment of a cleaning, sanitizing, or disinfecting scrubbing device, which consists of a non-thermal plasma generator and a moistened scrubbing material, worn on the feet.
Figure 9:
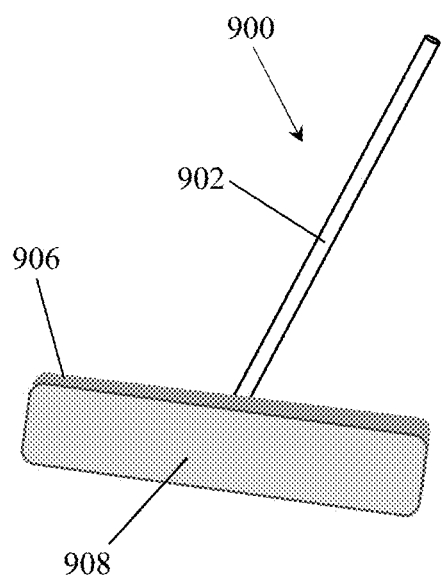
FIG. 9 is a schematic view of an exemplary embodiment of a cleaning, sanitizing, or disinfecting scrubbing device, which consists of a non-thermal plasma generator and a moistened scrubbing material, as a mop.
Figure 10:
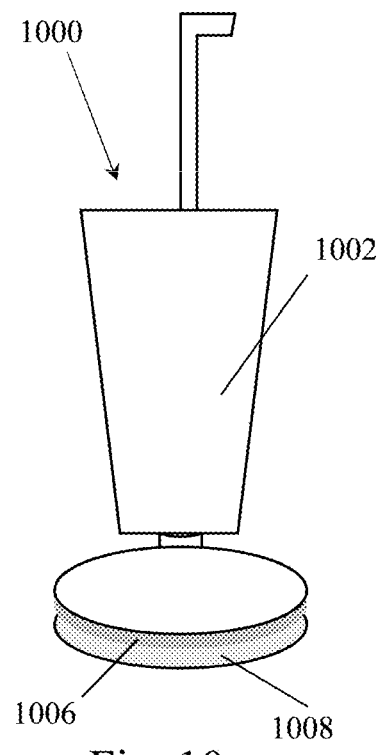
FIG. 10 is a schematic view of an exemplary embodiment of a cleaning, sanitizing, or disinfecting scrubbing device, which consists of a non-thermal plasma generator and a moistened scrubbing material, as a floor cleaner.

FIGS. 8-10 depict various other exemplary devices for cleaning, sanitizing or disinfecting a surface by wiping it with an activated fluid. Each of these exemplary devices includes similar features and utilizes the same basic principles as the above described mitt devices. For example, FIG. 8 shows an exemplary cleaning, sanitizing or disinfecting scrubbing device 800 that may be worn on the foot of a user. The device 800 includes a shoe, sock or boot 802, which may be any suitable shoe, sock or boot to be worn on the foot of a user. The shoe, sock or boot 802 may be made of any suitable material. In some embodiments the shoe, sock or boot 802 includes a plasma generator (not shown) (e.g., embedded in the sole of the shoe) for generating plasma 806 to active the fluid of an attached wipe 808. In some embodiments the device 800 includes a conductive mesh or perforated material (not shown) embedded in the wipe 808 or placed between the wipe 808 and the shoe, sock or boot 802. The device 800 may include spacers, power supplies, gas sources, or any other features described herein.

FIG. 9 shows an exemplary hand-held cleaning, sanitizing or disinfecting scrubbing device 900 that may be used to clean a floor, wall or ceiling surface. The device 900 includes a body 902, which may be any suitable length or material. The body 902 may include a handle and base that are connected. In some embodiments the body 902 includes a plasma generator (not shown) (e.g., embedded in the mop base) for generating plasma 906 to activate the fluid of an attached damp wipe 908. In some embodiments the device 900 includes a conductive mesh or perforated material (not shown) embedded in the wipe 908 or placed between the wipe 908 and the body 902. The device 900 may include spacers, power supplies, gas sources, or any other of the features described herein.

FIG. 10 shows an exemplary cleaning, sanitizing or disinfecting scrubbing device 1000 that may be used to clean a floor or other surface. The device 1000 includes a floor cleaner body 1002, which may be any suitable size. The base of the floor cleaner body 1002 may be rotatable as known in the art. In some embodiments the floor cleaning device 1000 is hand-held (e.g. with a handle). In some embodiments the floor cleaning device 1000 may have wheels (not shown) and be user-driven. In some embodiments the floor cleaner body 1002 includes a plasma generator (e.g., embedded in the rotatable base) for generating plasma 1006 to activate the fluid of an attached damp wipe 1008. In some embodiments the device 1000 includes a conductive mesh or perforated material (not shown) embedded in the wipe 1008 or placed between the wipe 1008 and the body 1002. The device 1000 may include spacers, power supplies, gas sources, or any other features disclosed herein.

Figure 11:
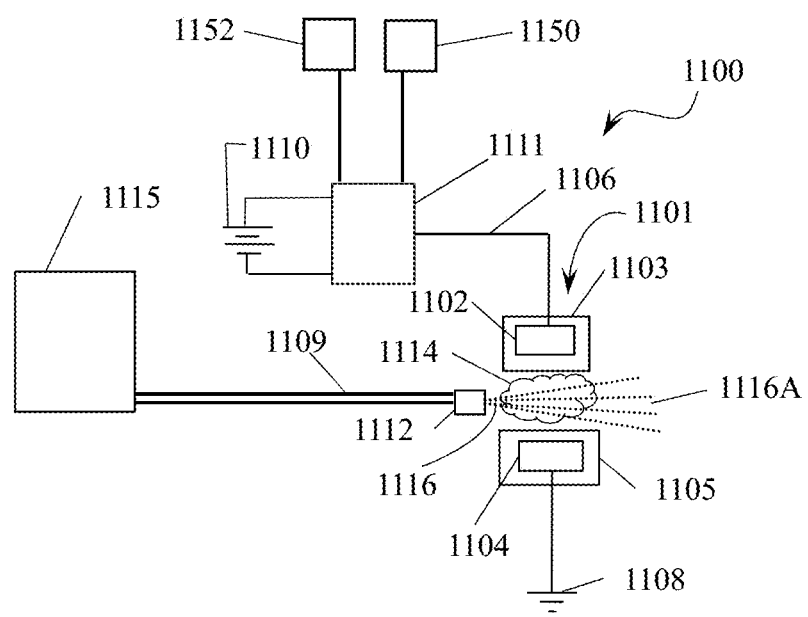
FIG. 11 is a schematic view of an exemplary embodiment of a non-thermal plasma activated fluid misting device.

FIG. 11 is a schematic view of an exemplary embodiment of a device 1100 for misting, activating and applying activated fluid on a surface that may be used in the various embodiments of cleaning devises disclosed herein. In the exemplary embodiment, device 1100 includes a reservoir 1115 for holding a fluid. The fluid may be, for example, water or ethanol. In some embodiments, the water contains an additive. In some embodiments the additive is an oil based additive, and accordingly must be dispersed throughout the water. In some embodiments, the reservoir 1115 is carried by a person and in such embodiments the movement of the person may aid in dispersing the additive throughout the water. Exemplary additives include, for example, cinnamaldehyde, isopropyl alcohol, and/or ethanol.

A tube or conduit 1109 extends from reservoir 1115 to misting element 1112. Misting element 1112 receives power through power and control circuitry 1111. In some embodiments, reservoir 1115 is located above the misting element 1112 and the misting element 1112 is gravity fed. In other embodiments, a pump (not shown) is positioned to pump the fluid from reservoir 1115 to the misting element 1112. Misting element 1112 outputs a liquid mist 1116.

The droplet or mist size of liquid mist 1116 can vary, and in some embodiments, is between about 50 micrometers and 3 millimeters in diameter. In some embodiments the diameter size is less than about 1 millimeter, and in some embodiments, it is less than about 500 micrometers. In some embodiments droplet diameter is less than about 250 micrometers, and in some embodiments, it is less than about 100 micrometers. The volume of the droplets or mist can vary and is between about 0.1 microliters to 500 microliters. In some embodiments the volume of the droplets or mist is less than about 250 microliters. In some embodiments, the volume of the droplets or mist is less than about 100 microliters, and in some embodiments the volume is less than about 10 microliters. In some embodiments, the mist is a vapor.

Device 1100 includes a plasma generator 1101. Plasma generator 1101 includes electrode 1102 which is connected to power and control circuitry 1111 and is surrounded by a dielectric barrier 1103. In this exemplary embodiment, power and control circuitry 1111 is powered by one or more batteries 1110, however, other sources of power, such as, for example a standard 120 VAC power receptacle may be used to provide power (not shown). Power and control circuitry 1111 is in circuit communication with DBD electrode 1102 through high voltage cable 1106.

A second electrode, electrode 1104 may also be at least partially surrounded by a dielectric barrier 1105. Dielectric barriers 1103, 1105 prevent arcing between electrode 1102 and electrode 1104, which is connected to a ground 1108. Dielectric barriers 1103, 1105 may include, for example, polymers, plastic, glass, ceramics or other known dielectric barriers. Power and control circuitry 1115 may have an output of, for example, about 20 kV at between about 0.5 kHz and 500 kHz. In one embodiment, the distance between electrodes 1102 and 1104 is between about 2 mm and several centimeters. Power and control circuitry 1115 may output high frequency AC power, RF power, pulsed DC power, pulsed AC power, a microwave power or the like. The power and control circuitry 1111 may include a power supply that can be pulsed with a duty cycle of 0-100% and in some embodiments, a pulse duration of 1 nanosecond up to 10 microseconds.

When electrode 1102 is energized, non-thermal plasma is generated between the electrodes 1102, 1104 by ionizing the gas located between the electrodes 1102, 1104. Fluid travels through conduit 1109 and through mister 1112. Mister 1112 may be, for example, a piezoelectric element, an atomizing nozzle or other mechanism that creates a mist or fine spray of fluid 1116. The mist or fine spray of fluid 1116 passes through the plasma 1114 and becomes plasma activated fluid 1116A, such as plasma activated water. The plasma activated fluid 1116A is charged and is attracted to electrically floating, or grounded, objects such as a surface (not shown) to be cleaned. In some embodiments, an advantage of the charged activated fluid 1116A is that the mist or fine spray of activated fluid does not become air born and necessitate the need for a user to where a respirator or mask to prevent activated fluid 1116A from being breathed in to a user's lungs.

The exemplary device 1100 includes an on/off switch 1150, which enables a user to turn on and off the device 1100. In some embodiments a sensor 1152 is included. Sensor 1152 may be, for example, a motion sensor, an accelerometer, one or more pressure sensors, or the like. In some embodiments, a user turns the device 1100 on using the on/off switch 1150 and when movement of device 1100 is detected by sensor 1152, the plasma generator 1101 generates plasma 1114 and the misting device 1112 delivers a mist or fine spray 1116 through the plasma 1114 to generate plasma activated fluid 1116A which is applied to the surface to decontaminate the surface (not shown). Any method of activating water or other formulations may be used in the present invention. Other exemplary methods of activating, water, or any of the formulations disclosed herein are identified above and are also shown and disclosed in co-owned U.S. Pat. No. 9,339,572 titled Methods and Solutions for Rapidly Killing or Deactivating Spores, which was file on Mar. 17, 2014, and Solutions and Methods of Making Solutions to kill or Deactivate Spores, Micro-Organisms, Bacteria and Fungus, patent publication number US 2014/055812 filed on Oct. 4, 2013. Both of which are incorporated herein by reference in their entirety.

Figure 12:
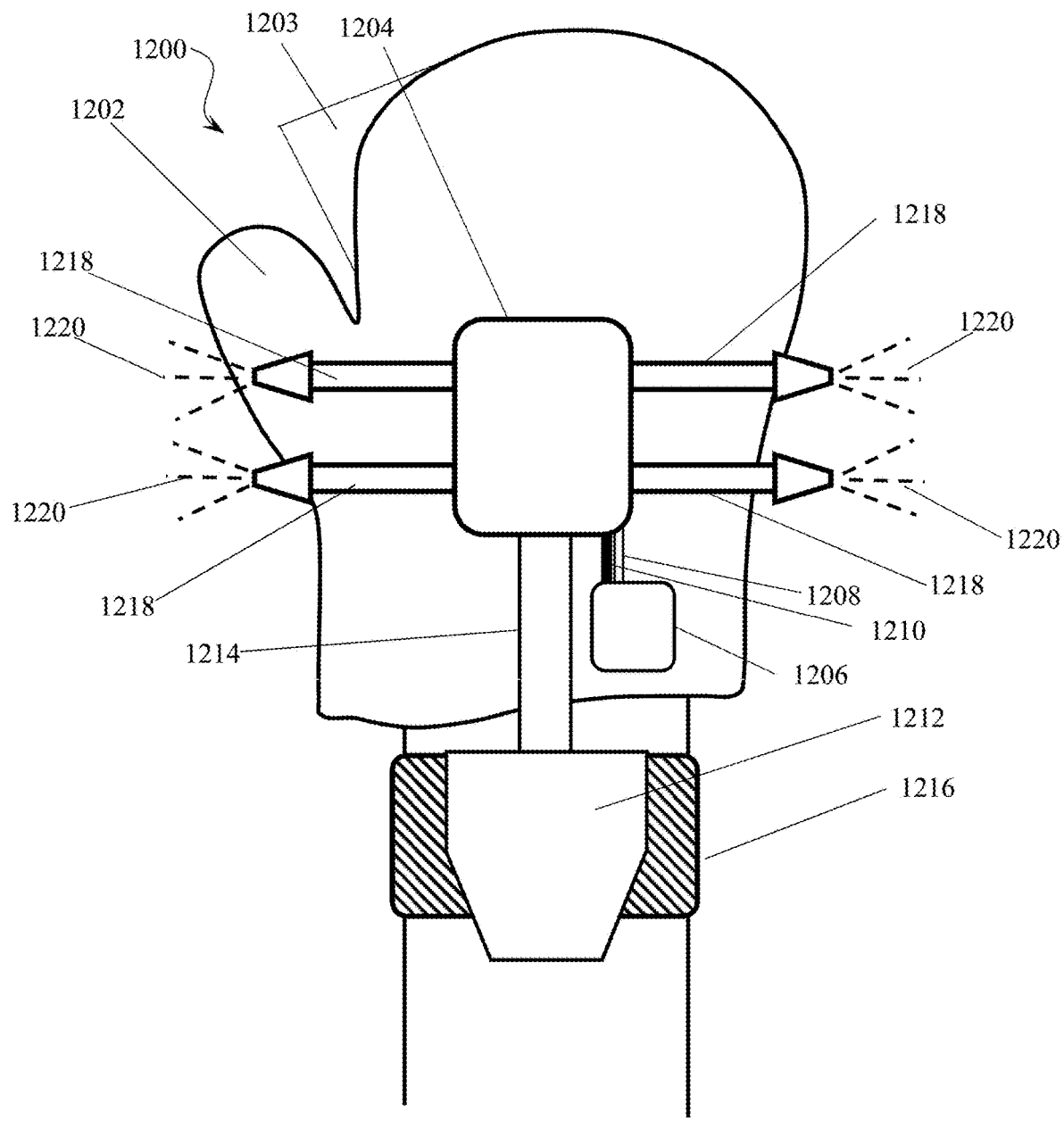
FIG. 12 is a schematic view of an exemplary embodiment of a cleaning, sanitizing, or disinfecting scrubbing mitt which delivers plasma activated fluid.

FIG. 12 illustrates an exemplary embodiment of a cleaning, sanitizing or disinfecting, scrubbing mitt 1200, which delivers plasma activated fluid. In some embodiments the mitt 1200 includes a thumb receiving member 1202. In some embodiments the mitt 1200 has a sock shape that covers all fingers of a hand. In some embodiments the mitt 1200 is made from a flexible material such as, for example, cloth, fabric, rubber, silicone, or combinations thereof. In some embodiments the interior surface of the mitt 1200 is made from a different material than the exterior surface. For example, a surface may be made from material that prevents gas or liquid from permeating the mitt 1200, while the interior surface may be made of a soft material so as to make the mitt 1200 more comfortable to wear. In some embodiments the exterior surface is made of, or has areas including, an abrasive material, for example steel wool or microfiber.

In some embodiments, the mitt 1200 includes a replaceable pad 1203. In some embodiments the replaceable scrubbing pad 1203, such as a wipe, is a soft absorbent material such as cloth, foamed polymer, or wood fiber. In some embodiments the replaceable scrubbing pad 1203 contains an abrasive material, for example steel wool or the like. In some embodiments, the scrubbing pad includes rubber, and in some embodiments the rubber forms one or more squeegees, one or more projections or the like. In some embodiments the replaceable pad 1203 includes a mix of one or more abrasive materials, rubber materials and absorbent materials. In some embodiments the replaceable pad 1203 is attachable to the bottom of the mitt 1200 with a strap. In some embodiments the replaceable pad 1203 is attachable to the bottom of the mitt 1200 using a hook and loop fastener, such as, for example Velcro®. In some embodiments, the replaceable pad 1203 is fastened to the mitt 1200 using one or more projections, clamps, or other securing means.

The mitt 1200 includes a plasma generator 1204. In some embodiments the plasma generator 1204 is mounted to the exterior surface of the mitt 1200. In some embodiments the plasma generator 1204 is mounted on the bottom of the mitt 1200 so as to be under the palm of a hand wearing the mitt 1200. In some embodiments the plasma generator 1204 is mounted to the top of the mitt 1200 so as to be over the back of a hand wearing the mitt 1200. In some embodiments the plasma generator 1204 is secured to the mitt 1200 by a strap or a fastener. In some embodiments the plasma generator 1204 is bonded to the mitt 1200 by an adhesive. In some embodiments the plasma generator 1204 is embedded (e.g., sewn or molded) into the mitt 1200.

The plasma generator 1204 may be of the same type or similar to the above-described embodiments for plasma generation. Thus, it may include one or more electrodes, one or more dielectric barriers, various electrode shapes and sizes, power and control circuitry, switches, sensors and the like. The plasma generator 1204 is powered by a battery unit 1206, however, other sources of power, such as, for example a standard 120 VAC power receptacle may be used to provide power (not shown). The battery unit 1206 may include one or more rechargeable batteries or disposable batteries. In some embodiments, the battery unit 1206 includes a battery receptacle mounted to or embedded in the mitt 1200, and rechargeable or disposable batteries are placed in the receptacle to power the plasma generator 1204. In some embodiments the battery unit 1206 includes a rechargeable battery, voltage regulation circuitry and a power input that are mounted to or embedded in the mitt 1200. In this embodiment, a power source can be plugged into the battery unit 1206 to charge to the battery or batteries within. In some embodiments, power and control circuitry is included in the battery unit 1206 instead of, or in addition to, the plasma generator 1204. The plasma generator 1204 is in circuit communication with battery unit 1206 through cables 1208 and 1210. Many of the components described herein, such as the battery 1206 and/or fluid reservoir 1212 may be mounted remotely on, for example, the user's back or on a cart.

The plasma generator 1204 of mitt 1200 includes a fluid reservoir 1212 for holding a fluid. Fluid reservoir 1212 may include a pump (not shown) for moving fluid from fluid reservoir 1212 to the plasma generator 1204. The fluid may be, for example, gas, such as air, or liquid, such as water and may include additives a described above. A tube or conduit 1214 extends from fluid reservoir 1212 to the plasma generator 1204. In some embodiments, the fluid reservoir 1212 is mounted on or embedded in the mitt 1200. In some embodiments the fluid reservoir 1212 is carried elsewhere by a person wearing the mitt 1200 or on a cart (not shown). For example, the reservoir 1212 may be attached to a wristband 1216 worn on the same arm as the mitt 1200. In some embodiments the fluid reservoir 1212 is worn on the back of the person wearing the mitt 1200. In some embodiments the fluid reservoir 1212 is carried by another person or is stationary, and the tube or conduit 1214 is sufficiently long to allow free movement of the mitt 1200.

Plasma generator 1204 creates plasma in an open area (not shown) inside and the fluid, in the form of a vapor, or liquid flows through the plasma or mixes with plasma-produced gas species to activate the fluid. Mitt 1200 further includes one or more dispersal tubes 1218 for dispersing activated fluid 1220 in a vapor, mist, or spray form. The mitt 1200 may include any number of dispersal tubes 1218, which may be arranged in any suitable orientation. For example, the mitt 1200 may have only one dispersal tube 1218 aimed to disperse activated fluid toward the front end to one side of the mitt 1200. The mitt 1200 may have multiple dispersal tubes 1218 aimed to the front, sides, or both of the mitt 1200. In one embodiment a plurality of dispersal tubes are oriented radially about the front and sides of the mitt 1200. In some embodiments the dispersal tube(s) 1218 are mounted on the bottom of the mitt 1200 so as to be under the palm of a hand wearing the mitt 1200. In some embodiments the dispersal tube(s) 1218 are mounted to the top of the mitt 1200 so as to be over the back of a hand wearing the mitt 1200. In some embodiments the dispersal tube(s) 1218 are secured to the mitt 1200 by a strap or a fastener. In some embodiments the dispersal tube(s) 1218 are bonded to the mitt 1200 by an adhesive. In some embodiments the dispersal tube(s) 1218 are embedded (e.g., sewn, molded) into the mitt 1200. In some embodiments, the mitt 1200 includes a wipe 1203 and the dispersal tube directs the activated fluid on the wipe (not shown). In some embodiments, the mitt 1200 includes a wipe 1203 and the dispersal tube directs the activated fluid to the surfaces to be cleaned, sanitized, or disinfected.

In some embodiments, a single fluid delivery element (not shown) in the plasma generator 1204 creates a mist or fine spray of fluid from the reservoir 1212. In a further embodiment, a single electrode or plurality of electrodes are disposed at one or more locations within the plasma generator 1204. The mist, spray, or vapor created by the fluid delivery element (not shown) is activated by the one or more electrodes and then flows out from the one or more dispersal tubes 1218. In some embodiments, each dispersal tube 1218 has an electrode (not shown) or group of electrodes in or near the dispersal tube 1218. Mist or spray from the fluid delivery element may thus be activated separately within each dispersal tube 1218. In another embodiment, the plasma generator 1204 includes separate fluid delivery elements and electrodes for each dispersal tube 1218. Mist or spray is created and activated individually at each dispersal tube. In some embodiments, fluid in a form of bulk liquid is activated in the plasma generator 1204 and then flows out from the one or more dispersal tubes 1218.

In some embodiments, the mitt 1200 includes an on/off switch (not shown), which enables a user to turn on and off the plasma generator 1204. In some embodiments one or more sensors (not shown) are included. The sensors may be, for example, motion sensors, accelerometers, gyroscope, pressure sensors, or the like and the fluid may be dispersed during movement of the mitt 1200. In some embodiments, a user turns the plasma generator 1204 on using the on/off switch and when movement of mitt 1200 is detected by a sensor, the plasma generator 1204 generates plasma activated fluid which is applied to a surface to decontaminate the surface (not shown). In some embodiments, the activated fluid is dispensed in front of the wiping action. In some embodiments activated fluid is dispensed downstream of the wiping action and left on the surface. In some embodiments, the motion sensors may trigger activated fluid dispersal when the mitt 1200 is moved laterally but not vertically. In some embodiments a pressure sensor detects when the mitt 1200 is pressed against a surface (not shown) and the plasma generator 1204 generates plasma activated fluid to decontaminate the surface.

The surface to which plasma activated fluid is applied may be any surface, including for example, surfaces in a hospital or nursing home such as, for example, table, a bed, etc. made of polymer, metal, rubber, glass, silicone, fabric material or the like. The surface may be a hard surface or a soft surface, such as, for example, linens, curtains and the like. In some embodiments, the surface may be skin or tissue.

Figure 13:
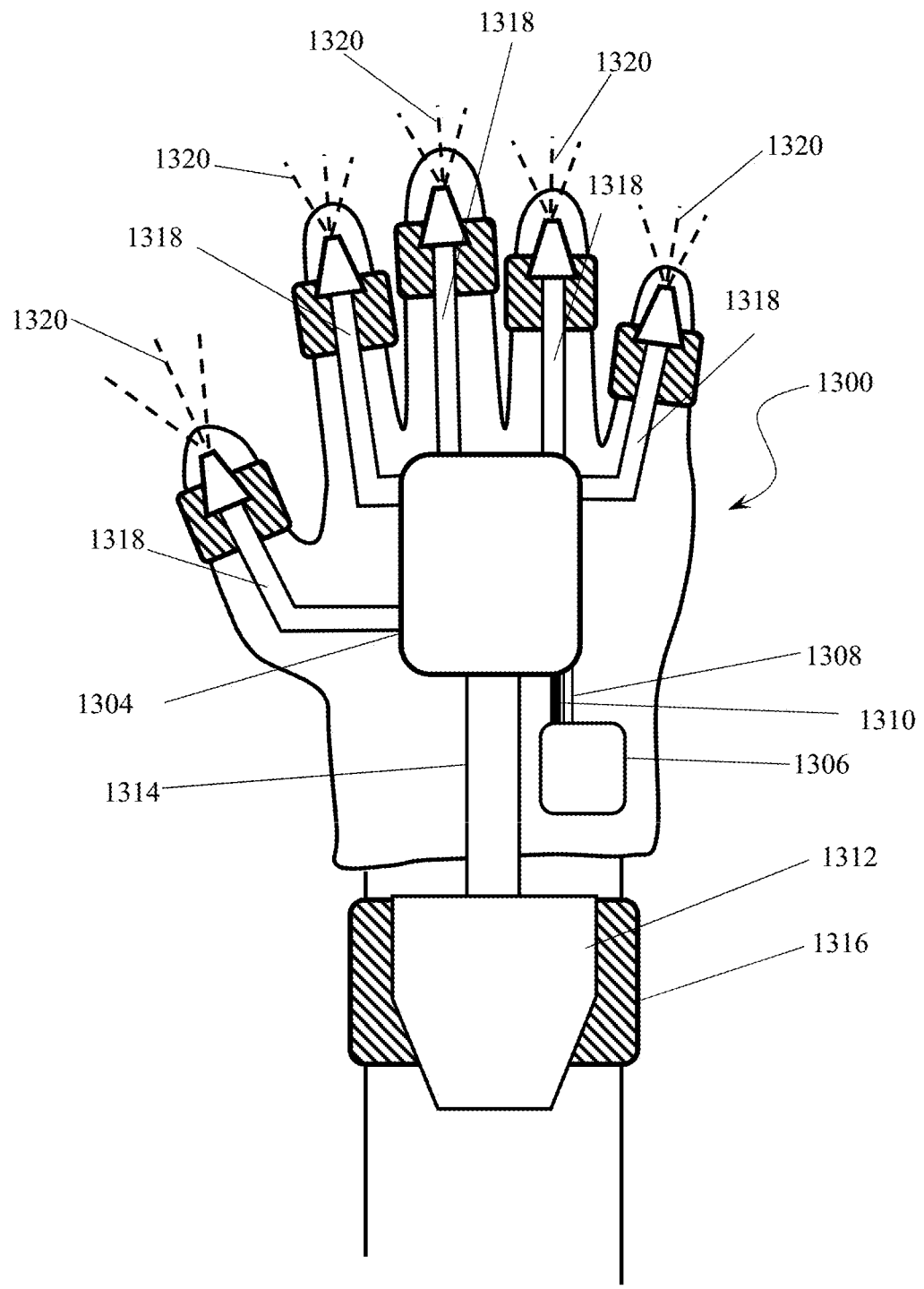
FIG. 13 is a schematic view of another exemplary embodiment of a cleaning, sanitizing, or disinfecting scrubbing glove which delivers plasma activated fluid.

FIG. 13 illustrates an exemplary embodiment of a cleaning, sanitizing or disinfecting, scrubbing glove 1300, which delivers plasma activated fluid. The glove 1300 has similar features to the mitt 1200 described above and may be made of, and or include any of the same materials. Like the mitt 1200, the glove 1300 includes a plasma generator 1304 and a battery unit 1306 electrically connected to the plasma generator 1304 via cables 1308 and 1310. A fluid reservoir 1312, illustrated in this exemplary embodiment as attached to a wristband 1316, is connected to plasma generator 1304 via a tube or conduit 1314. The glove may also include a replaceable scrubbing material, such as a wipe (not shown) attachable to the underside of the glove 1300.

Glove 1300 further includes one or more dispersal tubes 1318 for dispersing activated fluid 1320. The glove 1300 may include any number of dispersal tubes 1318, which may be arranged in any suitable orientation. In one embodiment, a dispersal tube 1318 is disposed on each finger of the glove 1300 and aimed to disperse activated fluid 1320 toward the front end each finger. In one embodiment the dispersal tubes 1318 are angled toward the outside of the glove 1300 to disperse activated fluid 1320 radially from the glove 1300. In some embodiments the dispersal tube(s) 1318 are mounted on the bottom of the glove 1300 so as to be under the palm and fingers of a hand wearing the glove 1300. In some embodiments the dispersal tube(s) 1318 are mounted to the top of the glove 1300 so as to be over the back of the fingers of a hand wearing the glove 1300. In some embodiments the dispersal tube(s) 1318 are secured to the glove 1300 by a strap or a fastener on each finger. In some embodiments the dispersal tube(s) 1318 are bonded to the fingers of glove 1300 by an adhesive. In some embodiments the dispersal tube(s) 1318 are embedded (e.g., sewn or molded) the fingers of glove 1300.

In some embodiments, a single fluid delivery element (not shown) in the plasma generator 1304 creates a mist, fine spray or vapor of fluid from the reservoir 1312. In a further embodiment, a single electrode or plurality of electrodes are disposed at one location in the plasma generator 1304. The mist or spray created by the fluid delivery element is activated by the one or more electrodes and then flows out from the one or more dispersal tubes 1318. In another embodiment, each dispersal tube 1318 has an electrode (not shown) or group of electrodes in or near the end of dispersal tube 1318. Mist or spray from the fluid delivery element is thus activated separately within each dispersal tube 1318 prior to dispersal of the activated fluid. In another embodiment, the plasma generator 1304 includes separate fluid delivery elements and electrodes for each dispersal tube 1318. Mist or spray is created and activated individually at each dispersal tube 1318. In some embodiments, fluid in a form of bulk liquid is activated in the plasma generator 1304 and then flows out from the one or more dispersal tubes 1318. Like the mitt 1200, the glove 1300 may include an on/off switch and one or more sensors to control fluid dispersal.

Figure 14:
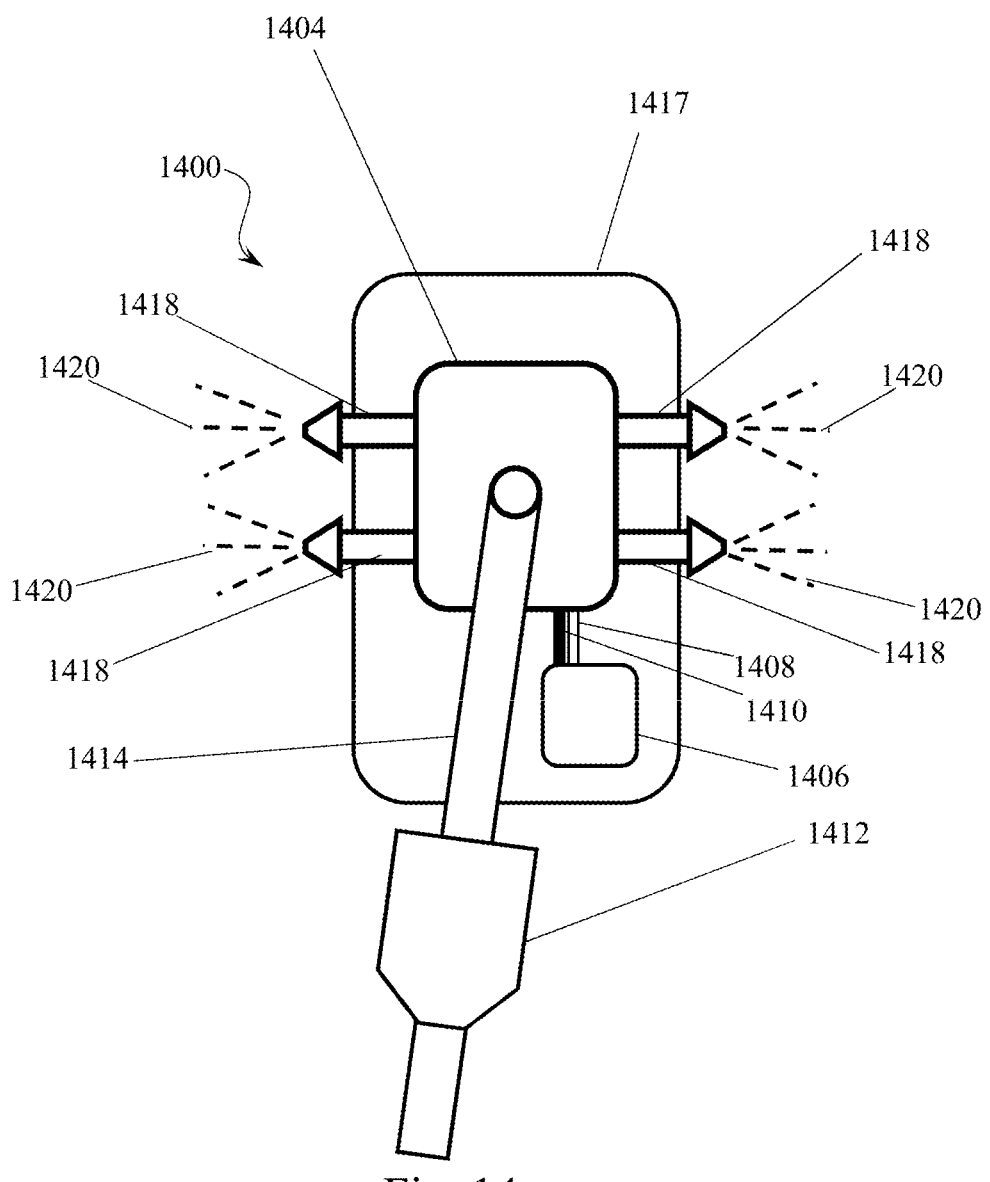
FIG. 14 is a schematic view of an exemplary embodiment of a handheld cleaning, sanitizing, or disinfecting scrubber which delivers plasma activated fluid.

FIG. 14 illustrates an exemplary embodiment of a handheld cleaning, sanitizing or disinfecting scrubber 1400, which delivers plasma activated fluid. The scrubber 1400 also has similar features to the mitt 1200 described above and may be made of any of the same materials. Like the mitt 1200, the scrubber 1400 includes a plasma generator 1404 and a battery unit 1406 electrically connected to the plasma generator 1404 via cables 1408 and 1410. A fluid reservoir 1412, is illustrated in this exemplary embodiment as attached to or part of a handle 1414. In one embodiment the reservoir 1412 is external to the scrubber 1400 (e.g., worn on the back of a user) and is attached to the plasma generator through a tube that extends through and out from the handle 1414. The scrubber 1400 may also include a replaceable scrubbing material 1417 attachable to the underside of the scrubber 1400.

Like the mitt 1200 and glove 1300, the scrubber 1400 may include any number of dispersal tubes 1418 for dispersing activated fluid 1420. The arrangement of the dispersal tubes 1418 and the placement of electrodes and misting elements relative to the dispersal tubes 1418 may be as described above for the other devices. The scrubber 1400 may similarly include an on/off switch and one or more sensors to control fluid dispersal.

While the present invention has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and/or illustrative examples shown and described. Accordingly, departures may be made from such details without departing from the spirit or scope of the applicants' general inventive concept.

We claim:

1. A device to clean, sanitize, or disinfect a surface to be cleaned using a fluid that is converted to an antimicrobial fluid comprising:
   a body configured to be movable by a person to clean a surface;
   a reservoir for holding a fluid;

a fluid;
wherein the fluid comprises water;
a pump for pumping the fluid to the body;
an applicator on the body for applying the fluid to one of the surface and a wipes substrate;
a non-thermal plasma generator for generating non-thermal plasma; and
wherein the non-thermal plasma generator is configured to generate non-thermal plasma in contact with the fluid, wherein contact with the non-thermal plasma changes the fluid to an activated fluid that includes one or more reactive species.

2. The device of claim 1 wherein the body has a scrubbing surface, and wherein the scrubbing surface is a wipes substrate.

3. The device of claim 2, wherein with the fluid is applied to the surface prior to the fluid being activated by non-thermal plasma.

4. The device of claim 1 wherein the fluid is applied to the surface after the fluid is activated by non-thermal plasma.

5. The device of claim 1 wherein the surface is moistened with the fluid prior to the fluid being activated by non-thermal plasma.

6. The device of claim 1 wherein the body is wearable by a user.

7. The device of claim 1 wherein the body is a mop.

8. The device of claim 1 wherein the body is a cleaning device having a rotatable head.

9. The device of claim 1 further comprising an array of spacer posts on the body, the array of spacer posts creating a space between the body and the surface to be cleaned.

10. The device of claim 9 further comprising a conductive mesh, wherein the conductive mesh is held between the body and the surface to be cleaned by the spacer posts.

11. The device of claim 1 wherein the body comprises a wipe and a conductive mesh.

12. The device of claim 1 further comprising a gas supply.

13. The device of claim 1 wherein the fluid comprises ethanol.

14. A device to clean, sanitize, or disinfect a surface to be cleaned using a fluid that is converted to an antimicrobial fluid comprising:
a body;
the body having a scrubbing surface, wherein the body is configured to be movable by a person to scrub a surface;
a non-thermal plasma generator for generating non-thermal plasma;
the non-thermal plasma generator comprising a high voltage electrode and a dielectric barrier; and
wherein the non-thermal plasma generator is configured to generate non-thermal plasma in contact with a fluid, wherein contact with the non-thermal plasma changes the fluid to an activated fluid that includes one or more reactive species; and
wherein the scrubbing surface is configured to be rubbed on the surface while the surface is contacted by the activated fluid having one or more reactive species.

15. The device of claim 14 further comprising a fluid reservoir in fluid communication with the body.

16. The device of claim 14 wherein the fluid is applied to the surface after the fluid is activated by non-thermal plasma.

17. The device of claim 14 wherein the fluid is applied to the surface prior to the fluid being activated by non-thermal plasma.

18. The device of claim 14 wherein the body is wearable by a user.

19. The device of claim 14 further comprising an array of spacer posts on the body, the array of spacer posts creating a space between the body and the surface to be cleaned.

20. The device of claim 14 further comprising a conductive mesh, wherein the conductive mesh is held between the body and the surface to be cleaned by the spacer posts.

* * * * *